(12) United States Patent
van Hemert et al.

(10) Patent No.: US 10,349,825 B2
(45) Date of Patent: Jul. 16, 2019

(54) IMAGING OF THE EYE

(71) Applicant: Optos PLC, Dunfermline, Scotland (GB)

(72) Inventors: Jano van Hemert, Edinburgh (GB); Michael Verhoek, Edinburgh (GB); David Brown, Houston, TX (US); Charles Wykoff, Houston, TX (US); Daniel Croft, Houston, TX (US)

(73) Assignee: Optos PLC, Dunfermline (GB)

( * ) Notice: Subject to any disclaimer, the term of this patent is extended or adjusted under 35 U.S.C. 154(b) by 341 days.

(21) Appl. No.: 15/308,028

(22) PCT Filed: May 1, 2015

(86) PCT No.: PCT/GB2015/051301
§ 371 (c)(1),
(2) Date: Oct. 31, 2016

(87) PCT Pub. No.: WO2015/166283
PCT Pub. Date: Nov. 5, 2015

(65) Prior Publication Data
US 2017/0049315 A1 Feb. 23, 2017

(30) Foreign Application Priority Data
May 2, 2014 (GB) .................................. 1407873.7

(51) Int. Cl.
*A61B 3/00* (2006.01)
*G06K 9/00* (2006.01)
(Continued)

(52) U.S. Cl.
CPC .......... *A61B 3/0025* (2013.01); *A61B 3/1005* (2013.01); *A61B 3/12* (2013.01);
(Continued)

(58) Field of Classification Search
USPC ........................................ 382/128, 131, 133
See application file for complete search history.

(56) References Cited

U.S. PATENT DOCUMENTS 7,453,472 B2 * 11/2008 Goede .................. G06F 17/241
345/634
8,134,554 B1 3/2012 Huang et al.
(Continued)

FOREIGN PATENT DOCUMENTS

| CN | 102884551 | 1/2013 |
|----|-----------|--------|
| WO | WO-2010/083381 | 7/2010 |
| WO | WO-2012/149480 | 11/2012 |

OTHER PUBLICATIONS

Office Action on Chinese Application No. 2015800219312 dated Apr. 10, 2018.
(Continued)

*Primary Examiner* — Ishrat I Sherali
(74) *Attorney, Agent, or Firm* — Pavan K. Agarwal; Shabbi S. Khan; Foley & Lardner LLP

(57) ABSTRACT

A method of determining a measurement of at least one cell type in an eye, comprising (i) obtaining a map of the cell type in the eye, (ii) obtaining a representation of the retina of the eye, (iii) matching the eye cell type map to the representation of the retina of the eye, (iv) defining a region of interest on the representation of the retina of the eye, (v) calculating a size of the region of interest on the representation of the retina of the eye, (vi) using the matched eye cell type map and the size of the region of interest to determine a measure of the cell type in the region of interest of the retina of the eye.

15 Claims, 3 Drawing Sheets

(51) Int. Cl.
*A61B 3/12* (2006.01)
*A61B 3/10* (2006.01)
*A61B 3/14* (2006.01)

(52) U.S. Cl.
CPC .............. *A61B 3/14* (2013.01); *G06K 9/0014* (2013.01); *G06K 9/0061* (2013.01); *A61B 3/102* (2013.01)

(56) References Cited

U.S. PATENT DOCUMENTS

| | | | | |
|---|---|---|---|---|
| 8,401,246 | B2* | 3/2013 | Huang | A61B 3/0058 351/206 |
| 9,649,031 | B2* | 5/2017 | Hemert | A61B 3/14 |
| 10,134,143 | B2* | 11/2018 | Hu | G06T 7/12 |
| 2006/0061595 | A1* | 3/2006 | Goede | G06F 17/241 345/619 |
| 2008/0007693 | A1* | 1/2008 | Williams | G06T 5/50 351/221 |
| 2009/0123036 | A1 | 5/2009 | Huang et al. | |
| 2010/0290005 | A1* | 11/2010 | Huang | A61B 3/102 351/206 |
| 2011/0007957 | A1* | 1/2011 | Sakagawa | A61B 3/102 382/131 |
| 2011/0080558 | A1 | 4/2011 | Marshall et al. | |
| 2013/0058553 | A1 | 3/2013 | Yonezawa et al. | |
| 2013/0071004 | A1* | 3/2013 | Yonezawa | G06K 9/0061 382/133 |
| 2014/0270444 | A1* | 9/2014 | Yang | G06T 7/0012 382/131 |

OTHER PUBLICATIONS

Christine A. Curcio et al.: "Human Photoreceptor Topography", dated Feb. 22, 1990.
Croft, Daniel: "IOVS: Quantification of Retinal Surface-Area from Montaged Ultra-Widefield Fundus Photography", dated Apr. 30, 2014.
International Search Report and Written Opinion for PCT/GB2015/051301 dated Sep. 1, 2015.
Office Action and Search Report for GB 1507565.8 dated Nov. 3, 2015.
Office Action on Chinese Application No. 201580021931.2 dated Sep. 1, 2017.

* cited by examiner

IMAGING OF THE EYE

RELATED APPLICATIONS

This application is a national stage application of International Patent Application Number PCT/GB2015/051301, which application claims priority to United Kingdom Patent Application GB 1407873.7. International Patent Application Number PCT/GB2015/051301 and United Kingdom Patent Application GB 1407873.7 are incorporated by reference.

The invention relates to improvements in and relating to imaging of the eye, particularly enhancing measurements of the retina of the eye with information derived from other cell types in the eye.

In retinal health care it can be beneficial to annotate one or portions of a retinal image which are of interest, e.g. due to disease or trauma, and take geometric measurements of the portions. For example, if a subject presents with a retina that has bleeding, it would be possible to annotate the area of bleeding and then calculate the size of the annotated area. The eye comprises various different cell types in the anterior segment of the eye. For example these may comprise retinal cells, such as photoreceptor cells required for human vision comprising rod cells (to see in low light and facilitate peripheral vision) and cone cells (to see colour), Müller cells, ganglion cells, bipolar cells, amacrine cells, horizontal cells and retinal pigment epithelial cells. For all of these cell types, the cells have a particular distribution throughout the eye. For example, cone cells are mainly concentrated on the fovea, which is where the central vision focuses, whereas rod cells are more widely distributed with a decrease at the fovea to make room for the cone cells. It is possible to measure information concerning the distribution of the eye cell types. This information can be combined with measurement information of a portion of interest of a retina, e.g. a lesion, to enhance the usefulness of the measurement information of the retinal portion of interest.

According to a first aspect of the invention there is provided a method of determining a measurement of at least one cell type in an eye, comprising
(i) obtaining a map of the cell type in the eye,
(ii) obtaining a representation of the retina of the eye,
(iii) matching the eye cell type map to the representation of the retina of the eye,
(iv) defining a region of interest on the representation of the retina of the eye,
(v) calculating a size of the region of interest on the representation of the retina of the eye,
(vi) using the matched eye cell type map and the size of the region of interest to determine a measure of the cell type in the region of interest of the retina of the eye.

The cell type in the eye may comprise a cell type in the posterior segment of the eye. The cell type in the posterior segment of the eye may comprise a retinal cell type. The retinal cell type may comprise any of photoreceptor cells such as rod cells or cone cells, Müller cells, ganglion cells, bipolar cells, amacrine cells, horizontal cells and retinal pigment epithelial cells.

Obtaining the eye cell type map may comprise measuring the cell type in the eye. Obtaining the eye cell type map may comprise using cell type data obtained from donor eyes. Obtaining the eye cell type map may comprise interpolation and extrapolation of the cell type data. Obtaining the eye cell type map may comprise receiving at least one previously-produced eye cell type map.

The eye cell type map may comprise a cell type distribution map. The eye cell type map may comprise a cell type density map. The eye cell type map may comprise a two dimensional map. The eye cell type map may comprise a three dimensional map.

The representation of the retina of the eye may comprise a representation of a portion of the retina of the eye. The representation of the retina of the eye may comprise a two dimensional representation. The representation of the retina of the eye may comprise a three dimensional representation.

Obtaining the representation of the retina of the eye may comprise obtaining a two dimensional acquired representation by operating an imaging device. Obtaining the representation of the retina of the eye may comprise receiving a two dimensional acquired representation previously obtained by an imaging device. The imaging device may be an ophthalmoscope such as a scanning laser ophthalmoscope, particularly a wide field scanning laser ophthalmoscope. The imaging device may be a fundus camera. The imaging device may be an optical coherence tomography device.

Obtaining the representation of the retina of the eye may comprise obtaining a three dimensional generated representation converted from a two dimensional acquired representation. Obtaining the representation of the retina of the eye may comprise obtaining a two dimensional regenerated representation converted from a three dimensional generated representation.

Matching the eye cell type map to the representation of the retina of the eye may comprise matching a two dimensional eye cell type map to a two dimensional acquired representation. Matching the eye cell type map to the representation of the retina of the eye may comprise matching a three dimensional eye cell type map to a three dimensional generated representation. Matching the eye cell type map to the representation of the retina of the eye may comprise matching a two dimensional eye cell type map to a two dimensional regenerated representation.

Matching the eye cell type map to the representation of the retina of the eye may comprise matching coordinate systems of the map and the representation. Additionally or alternatively, matching the eye cell type map to the representation of the retina of the eye may comprise overlaying corresponding features of the map and the representation.

Defining a region of interest on the representation of the retina of the eye may comprise choosing one or more coordinates of the representation to demarcate the region of interest. The one or more coordinates of the representation may define one or more points on the representation. The or each point on the representation may be identified on a screen using a pointing device such as a mouse.

Defining a region of interest on the representation of the retina of the eye may comprise using coordinates of a plurality of points on the representation to demarcate an area region of interest. The area region of interest may outline a structure on the representation of the retina of the eye. The structure may comprise, for example, an inherent structure of the retina such as the fovea or a disease structure of the retina such as a lesion, tumour, oedema, etc.

Defining a region of interest on the representation of the retina of the eye may comprise using coordinates of first and second points on the representation to demarcate a distance region of interest. The distance region of interest may follow a structure on the representation of the retina of the eye. The structure may comprise, for example, an inherent structure of the retina such as a blood vessel or a disease structure of the retina such as a lesion, etc.

Calculating a size of the region of interest on the representation of the retina of the eye may comprise obtaining a two dimensional representation of the retina of the eye, deriving a geometrical remapping which converts the two dimensional representation of the retina to a three dimensional representation of the retina, using one or more coordinates of the two dimensional representation of the retina to demarcate the region of interest on the two dimensional representation, using the geometrical remapping to convert the or each coordinate of the two dimensional representation of the retina to an equivalent coordinate of the three dimensional representation of the retina, and using the or each equivalent coordinate of the three dimensional representation of the retina to calculate the size of the region of interest.

Using the matched eye cell type map and the size of the region of interest to determine a measure of the cell type in the region of interest of the retina of the eye may comprise counting the number of the cell type in the region of interest. Using the matched eye cell type map and the size of the region of interest to determine a measure of the cell type in the region of interest of the retina of the eye may comprise calculating the density of the cell type in the region of interest.

The measure of the cell type in the region of interest of the retina of the eye may be output to a user. The measure of the cell type in the region of interest of the retina of the eye may be represented on the representation of the retina of the eye.

According to a second aspect of the invention there is provided a computer readable media storing program instructions which, when executed, perform the method of the first aspect of the invention.

According to a third aspect of the invention there is provided a system for determining a measurement of at least one cell type in an eye, comprising a mapping element which obtains a map of the eye cell type, a representation element which obtains a representation of the retina of the eye, a matching element which matches the eye cell type map to the representation of the retina of the eye, a definition element which defines a region of interest on the representation of the retina of the eye, a sizing element which calculates a size of the region of interest on the representation of the retina of the eye, and a determination element which uses the matched eye cell type map and the size of the region of interest to determine a measure of the eye cell type in the region of interest of the retina of the eye.

When medical practitioners or researchers measure the size of a structure, e.g. a lesion, on a retinal representation, the invention enhances that measurement with the impact the location and size of the lesion has on the number of cells of the eye cell type. For example, when the eye cell type comprises photoreceptor cells and the invention determines that many cells of this cell type are affected by pathology, this may translate to impaired vision.

An embodiment of the invention will now be described by way of example only with reference to the accompanying drawings, in which.

Figure 1:
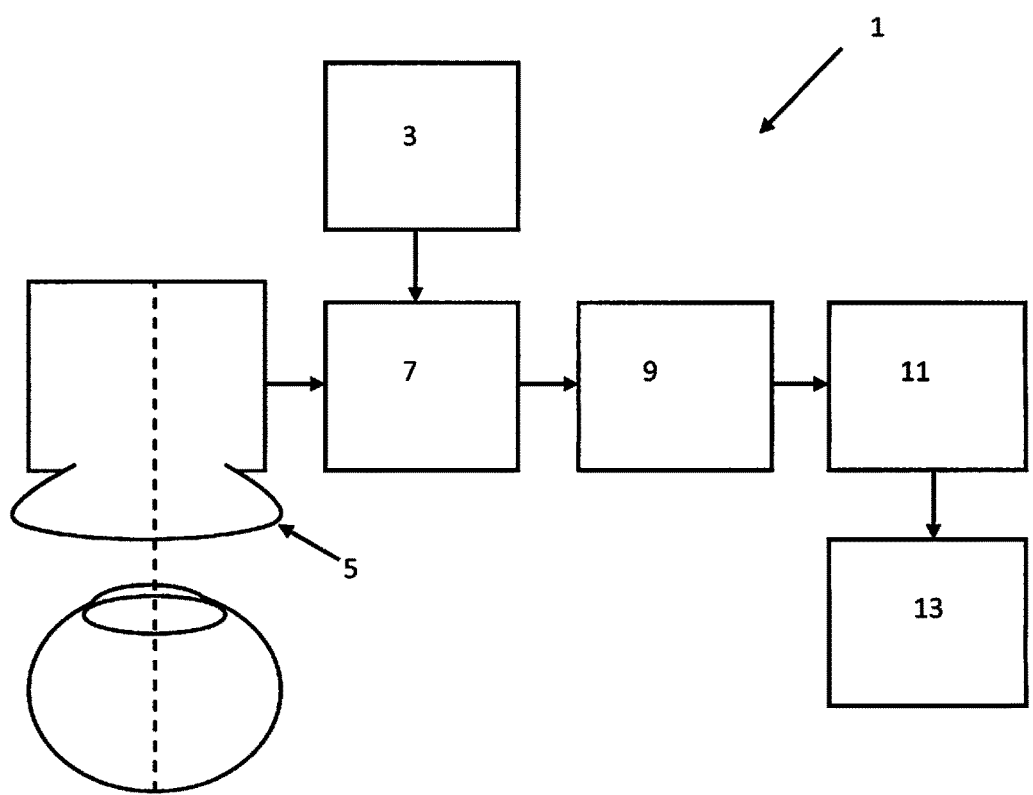
FIG. 1 is a schematic representation of a system for determining a measurement of at least one cell type in an eye according to the third aspect of the invention.

Referring to FIG. 1, the system 1 for determining a measurement of at least one cell type in an eye, comprises a mapping element 3 which obtains a map of the eye cell type, a representation element 5 which obtains a representation of the retina of the eye, a matching element 7 which matches the eye cell type map to the representation of the retina of the eye, a definition element 9 which defines a region of interest on the representation of the retina of the eye, a sizing element 11 which calculates a size of the region of interest on the representation of the retina of the eye, and a determination element 13 which uses the matched eye cell type map and the size of the region of interest to determine a measure of the eye cell type in the region of interest of the retina of the eye. The system 1 uses the computer readable media of the second aspect of the invention, which stores program instructions which, when executed, perform the method of the first aspect of the invention. Although the various elements of the system 1 are shown as separate elements, it will be appreciated that two or more of the elements may be provided together, for example as a processor which runs the program instructions to carry out the method.

Figure 2:
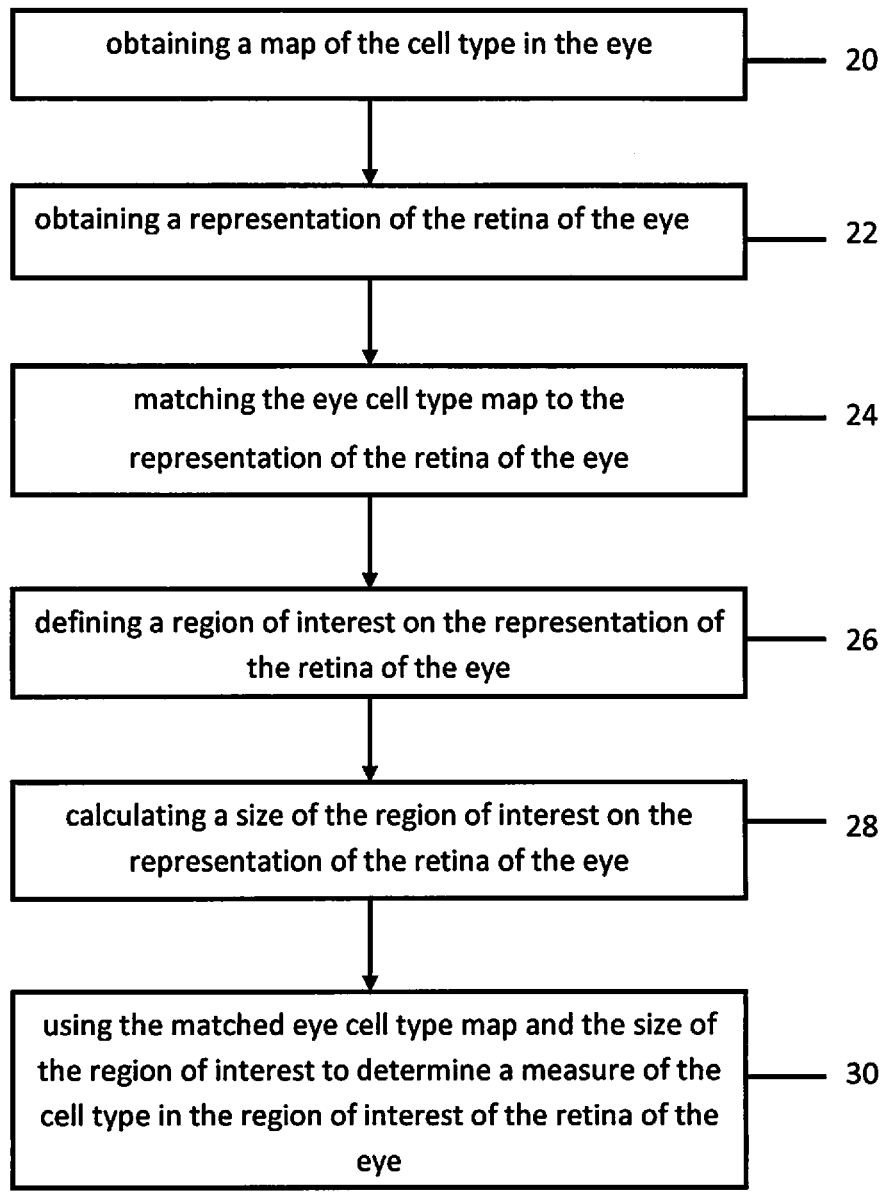
FIG. 2 is a schematic representation of a method of determining a measurement of at least one cell type in an eye according to the first aspect of the invention.

The system 1 carries out the method of the first aspect of the invention, shown in FIG. 2. The method of determining a measurement of at least one cell type in an eye comprises obtaining a map of the cell type in the eye (20), obtaining a representation of the retina of the eye (22), matching the eye cell type map to the representation of the retina of the eye (24), defining a region of interest on the representation of the retina of the eye (26), calculating a size of the region of interest on the representation of the retina of the eye (28), and using the matched eye cell type map and the size of the region of interest to determine a measure of the cell type in the region of interest of the retina of the eye (30).

In this embodiment, the eye cell type comprise photoreceptor cells comprising rod cells and cone cells, but it will be appreciated that the system and method apply to other eye cell types.

Obtaining the eye cell type map (20) comprises using the mapping element 3 of the system 1 to measure the rod cells and the cone cells in the eye. The eye cell type map comprises a two dimensional density map of the rod cells and the cone cells.

The representation element 5 of the system 1 comprises an imaging device which, in this embodiment, is a wide field scanning laser ophthalmoscope. The representation element 5 is used to obtain the representation of the retina of the eye comprising a two dimensional representation of a portion of the retina of the eye.

The matching element 7 of the system 1 is used to match the two dimensional density map of the rod cells and the cone cells to the two dimensional acquired representation of the portion of the retina of the eye. The matching comprises overlaying corresponding features of the density map and the representation.

A user of the system 1, such as a physician, uses the definition element 9 to define a region of interest on the representation of the portion of the retina of the eye. The definition element 9 comprises a screen and a mouse (not shown). The retinal portion representation is displayed to the user on the screen and the user uses the mouse to identify a plurality of points on the representation which denote a plurality of coordinates of the representation which demarcate the region of interest. The coordinates of the plurality of points on the representation demarcate an area region of interest, which outlines a structure on the representation of the retina of the eye, for example, an inherent structure of the retina such as the fovea or a disease structure of the retina such as a lesion, tumour, oedema, etc.

The sizing element 11 of the system 1 is used to calculate the size of the region of interest. This comprises obtaining a two dimensional representation of the retina of the eye, deriving a geometrical remapping which converts the two dimensional representation of the retina to a three dimensional representation of the retina, using one or more coordinates of the two dimensional representation of the retina to demarcate the region of interest on the two dimensional representation, using the geometrical remapping to convert the or each coordinate of the two dimensional representation of the retina to an equivalent coordinate of the three dimensional representation of the retina, and using the or each equivalent coordinate of the three dimensional representation of the retina to calculate the size of the region of interest.

The determination element 13 of the system 1 is then used to determine a measure of the rod cells and the cone cells in the region of interest of the retina of the eye, using the matched rod and cone density map and the size of the region of interest. This comprises calculating the density of the rod cells and the density of the cone cells in the region of interest. The measure of the rod cells and the cone cells in the region of interest of the retina of the eye is output to the user. The measure of the rod cells and the cone cells in the region of interest can then be used to infer information concerning the health of the eye.

Figure 3:
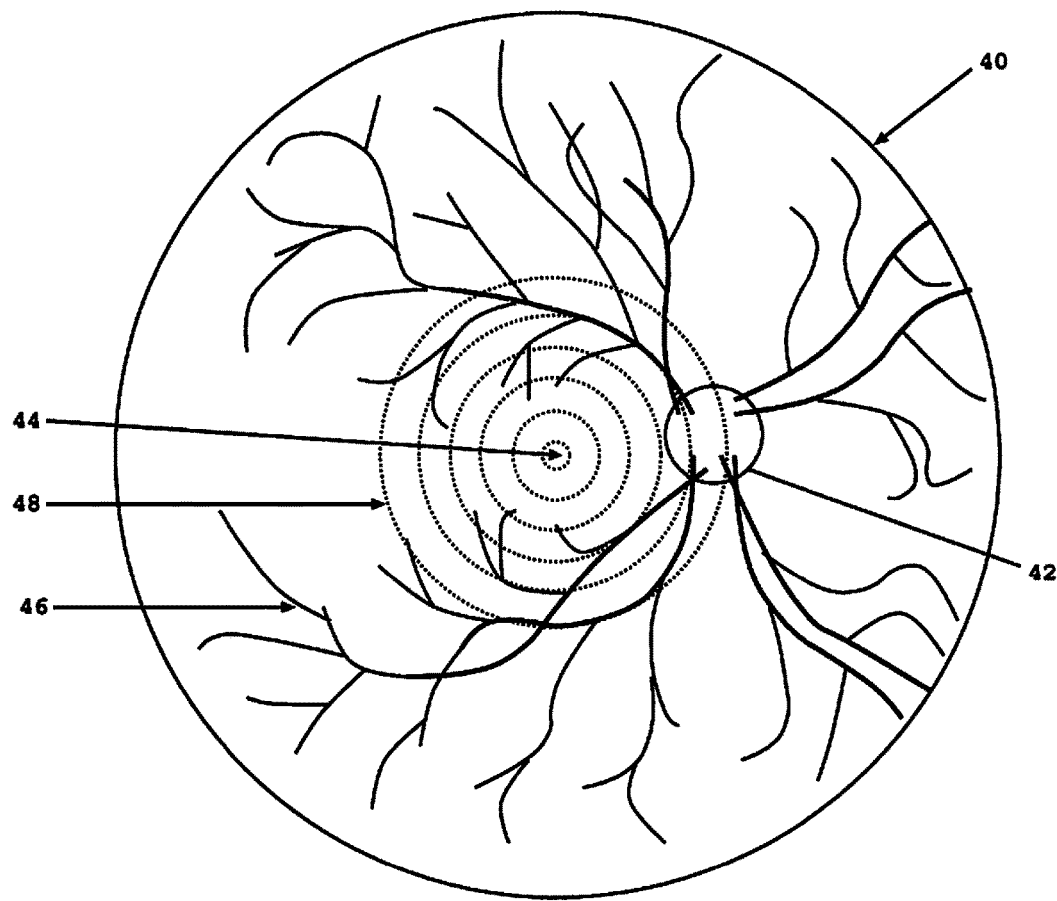
FIG. 3 is a schematic representation of a matched eye cell type map and a representation of a retina of an eye obtained using the system of FIG. 1 and the method of FIG. 2.

FIG. 3 shows a representation 40 of portion of a retina of an eye, obtained using the representation element 5 of the system 1. The representation 40 comprises a two dimensional representation of the portion of the retina of the eye comprising optic nerve head 42, fovea 44 and retinal vasculature 46. The figure further shows an eye cell type map 48, obtained using the mapping element 3 of the system 1. The eye cell type map 48 comprises a two dimensional density map of the rod cells and the cone cells in the eye. The rod and cone cell density map 48 comprises a series of concentric regions, each region having a different density of rod and cone cells, with the innermost region having the highest density of the rod and cone cells and the outermost region having the lowest density of the rod and cone cells. The retina representation 40 and the rod and cone cell density map 48 have been matched using the matching element 7 of the system 1, by overlaying corresponding features, in this case the fovea, of the representation 40 and the density map 48.

The retina representation 40 and the rod and cone cell density map 48 are displayed to the user of the system 1, such as a physician. The user can then use the definition element 9 to define a region of interest on the representation 40 of the portion of the retina of the eye, for example, an inherent structure of the retina such as the fovea 44 or a disease structure of the retina such as a lesion, tumour, oedema, etc. The sizing element 11 of the system 1 is used to calculate the size of the region of interest. The determination element 13 of the system 1 is then used to determine the density of the rod cells and the cone cells in the region of interest of the retina of the eye, using the matched rod and cone density map 48 and the size of the region of interest on the retina representation 40. The density of the rod cells and the cone cells in the region of interest of the retina of the eye is output to the user and used to infer information concerning the health of the eye.

The invention claimed is:

1. A method of determining a measurement of at least one cell type in an eye, comprising
   (i) obtaining, by one or more processors, a map of the cell type in the eye;
   (ii) obtaining, by the one or more processors, a representation of the retina of the eye;
   (iii) matching, by the one or more processors, the eye cell type map to the representation of the retina of the eye;
   (iv) defining, by the one or more processors, a region of interest on the representation of the retina of the eye;
   (v) calculating, by the one or more processors, a size of the region of interest on the representation of the retina of the eye;
   (vi) using, by one or more processors, the matched eye cell type map and the size of the region of interest to determine a measure of the cell type in the region of interest of the retina of the eye; and
   (vii) outputting, by the one or more processors, the determined measure of the cell type in the region of interest of the retina of the eye to provide a user with information indicative of the health of the eye.

2. The method of claim 1 in which the cell type in the eye comprises a cell type in the posterior segment of the eye.

3. The method of claim 2 in which the cell type in the posterior segment of the eye comprises a retinal cell type.

4. The method of claim 3 in which the retinal cell type comprises any of photoreceptor cells such as rod cells or cone cells, Muller cells, ganglion cells, bipolar cells, amacrine cells, horizontal cells and retinal pigment epithelial cells.

5. The method of claim 1, wherein obtaining the eye cell type map comprises measuring the cell type in the eye.

6. The method of claim 1, wherein the eye cell type map comprises any of a cell type distribution map, a cell type density map.

7. The method of claim 1, wherein the matching the eye cell type map to the representation of the retina of the eye comprises matching coordinate systems of the map and the representation.

8. The method of claim 1, wherein matching the eye cell type map to the representation of the retina of the eye comprises overlaying corresponding features of the map and the representation.

9. The method of claim 1, wherein defining a region of interest on the representation of the retina of the eye comprises choosing one or more coordinates of the representation to demarcate the region of interest.

10. The method of claim 1, wherein defining a region of interest on the representation of the retina of the eye comprises using coordinates of a plurality of points on the representation to demarcate an area region of interest.

11. The method of claim 1, wherein calculating a size of the region of interest on the representation of the retina of the eye comprises;
    obtaining a two dimensional representation of the retina of the eye,
    deriving, by the one or more processors, a geometrical remapping which converts the two dimensional representation of the retina to a three dimensional representation of the retina,
    using, by the one or more processors, one or more coordinates of the two dimensional representation of the retina to demarcate the region of interest on the two dimensional representation,
    converting, by the one or more processors using the geometrical remapping, each coordinate of the one or more coordinates of the two dimensional representation of the retina to an equivalent coordinate of the three dimensional representation of the retina, and using each equivalent coordinate of the three dimensional representation of the retina to calculate the size of the region of interest.

12. The method of claim 1, using the matched eye cell type map and the size of the region of interest to determine a measure of the cell type in the region of interest of the retina of the eye comprises counting the number of the cell type in the region of interest.

13. The method of claim 1, using the matched eye cell type map and the size of the region of interest to determine a measure of the cell type in the region of interest of the retina of the eye comprises calculating the density of the cell type in the region of interest.

14. A non-transitory computer readable media storing program instructions which, when executed by one or more processors, causes the one or more processors to:
   (i) obtain a map of the cell type in the eye;
   (ii) obtain a representation of the retina of the eye;
   (iii) match the eye cell type map to the representation of the retina of the eye;
   (iv) define a region of interest on the representation of the retina of the eye;
   (v) calculate a size of the region of interest on the representation of the retina of the eye;
   (vi) use the matched eye cell type map and the size of the region of interest to determine a measure of the cell type in the region of interest of the retina of the eye; and
   (vii) output the determined measure of the cell type in the region of interest of the retina of the eye to provide a user with information indicative of the health of the eye.

15. A system for determining a measurement of at least one cell type in an eye, comprising:
   one or more processors coupled to a memory, the one or more processors configured to:
   obtain a map of the eye cell type,
   obtain a representation of the retina of the eye,
   match the eye cell type map to the representation of the retina of the eye,
   define a region of interest on the representation of the retina of the eye,
   calculate a size of the region of interest on the representation of the retina of the eye,
   use the matched eye cell type map and the size of the region of interest to determine a measure of the eye cell type in the region of interest of the retina of the eye, and
   output the determined measure of the cell type in the region of interest of the retina of the eye to provide a user with information indicative of the health of the eye.

* * * * *